US008877170B2

(12) United States Patent
Ladet et al.

(10) Patent No.: US 8,877,170 B2
(45) Date of Patent: Nov. 4, 2014

(54) MEDICAL DEVICE WITH INFLAMMATORY RESPONSE-REDUCING COATING (75) Inventors: Sebastien Ladet, Lyons (FR); Philippe Gravagna, Irigny (FR)

(73) Assignee: Sofradim Production (FR)

( * ) Notice: Subject to any disclaimer, the term of this patent is extended or adjusted under 35 U.S.C. 154(b) by 601 days.

(21) Appl. No.: 12/708,861

(22) Filed: Feb. 19, 2010

(65) Prior Publication Data

US 2010/0215709 A1 Aug. 26, 2010

Related U.S. Application Data (60) Provisional application No. 61/154,385, filed on Feb. 21, 2009.

(51) Int. Cl.
| | | |
|---|---|---|
| A61L 31/10 | (2006.01) | |
| A61L 33/08 | (2006.01) | |
| A61L 33/00 | (2006.01) | |
| C08B 37/08 | (2006.01) | |
| C08L 5/08 | (2006.01) | |
| A61L 31/16 | (2006.01) | |
| A61L 17/14 | (2006.01) | |
| A61L 17/00 | (2006.01) | |

(52) U.S. Cl.
CPC ............. A61L 17/005 (2013.01); A61L 31/16 (2013.01); A61L 17/145 (2013.01); A61L 2300/606 (2013.01); A61L 2300/43 (2013.01); A61L 2300/256 (2013.01); A61L 2300/41 (2013.01); A61L 31/10 (2013.01); A61L 2300/414 (2013.01); A61L 2300/406 (2013.01); A61L 2300/252 (2013.01)
USPC .......... 424/78.17; 424/422; 424/423; 514/55; 536/20; 106/162.2

(58) Field of Classification Search
CPC ..... A61L 31/10; A61L 33/0088; A61L 33/08; C08B 37/003; C08L 5/08
See application file for complete search history.

(56) References Cited

U.S. PATENT DOCUMENTS

| | | | |
|---|---|---|---|
| 3,767,085 A | 10/1973 | Cannon et al. | |
| 4,326,532 A * | 4/1982 | Hammar | 604/266 |
| 4,359,049 A | 11/1982 | Redl et al. | |
| 4,538,920 A | 9/1985 | Drake | |
| 4,753,536 A | 6/1988 | Spehar et al. | |
| 4,839,345 A | 6/1989 | Doi et al. | |
| 4,857,403 A | 8/1989 | De Lucca et al. | |
| 4,880,662 A | 11/1989 | Habrich et al. | |
| 5,372,585 A | 12/1994 | Tiefenbrun et al. | |
| 5,562,946 A | 10/1996 | Fofonoff et al. | |
| 5,578,662 A | 11/1996 | Bennett et al. | |
| 5,582,955 A | 12/1996 | Keana et al. | |
| 5,612,050 A | 3/1997 | Rowe et al. | |
| 5,911,942 A | 6/1999 | Fofonoff et al. | |
| 6,107,365 A | 8/2000 | Bertozzi et al. | |
| 6,107,453 A | 8/2000 | Zuccato et al. | |
| 6,251,959 B1 * | 6/2001 | Kawahara et al. | 516/67 |
| 6,451,032 B1 | 9/2002 | Ory et al. | |
| 6,534,611 B1 | 3/2003 | Darling et al. | |
| 6,552,103 B1 | 4/2003 | Bertozzi et al. | |
| 6,570,040 B2 | 5/2003 | Saxon et al. | |
| 6,576,000 B2 | 6/2003 | Carrison | |
| 6,806,260 B1 * | 10/2004 | Hirofumi et al. | 514/55 |
| 6,881,766 B2 | 4/2005 | Hain | |
| 7,012,126 B2 | 3/2006 | Matsuda et al. | |
| 7,105,629 B2 | 9/2006 | Matsuda et al. | |
| 7,122,703 B2 | 10/2006 | Saxon et al. | |
| 7,144,976 B2 | 12/2006 | Matsuda et al. | |
| 7,172,877 B2 | 2/2007 | Ting | |
| 7,247,692 B2 | 7/2007 | Laredo | |
| 7,294,357 B2 | 11/2007 | Roby | |
| 7,371,719 B2 | 5/2008 | Stupp et al. | |
| 7,375,234 B2 | 5/2008 | Sharpless et al. | |
| 7,618,944 B2 | 11/2009 | Breitenkamp et al. | |
| 7,650,588 B2 | 1/2010 | Ivansen | |
| 7,667,012 B2 | 2/2010 | Saxon et al. | |
| 2002/0016003 A1 | 2/2002 | Saxon et al. | |
| 2002/0161170 A1 | 10/2002 | Matsuda et al. | |
| 2002/0169275 A1 | 11/2002 | Matsuda et al. | |
| 2002/0173616 A1 | 11/2002 | Matsuda et al. | |
| 2003/0100086 A1 | 5/2003 | Yao et al. | |
| 2003/0135238 A1 | 7/2003 | Milbocker | |
| 2003/0199084 A1 | 10/2003 | Saxon et al. | |
| 2003/0205454 A1 | 11/2003 | Hlavinka et al. | |
| 2003/0215801 A1 | 11/2003 | Pieken et al. | |
| 2004/0170752 A1 | 9/2004 | Luthra et al. | |

(Continued)

FOREIGN PATENT DOCUMENTS

| | | | |
|---|---|---|---|
| EP | 0077098 A2 | 4/1983 | |
| EP | 0328050 A2 | 8/1989 | |

(Continued)

OTHER PUBLICATIONS

Goycoolea et al., Effect of Molecular Weight and Degree of Acetylation on the Physicochemical Characteristics of Chitosan Nanoparticles, 8th International Conference of the European Chitin Society (EUCHIS '07) Sep. 10, 2007.*

Tomihata et al. In vitro and in vivo degradation of films of chitin and its deacetylated derivatives. Biomaterials 18 (1997) 567-575.*

Han et al. Preparation and surface characterization of PEO-grafted and heparin-immobilized polyurethanes. J. Biomed. Mater. Res.: Applied Biomaterials, vol. 23, No. A1, 87-104 (1989).*

Aiba, S. Studies on chitosan: 3. Evidence for the presence of random and block copolymer structures in partially N-acetylated chitosans. Int. J. Biol. Macromol., 1991, vol. 13, pp. 40-44.*

Binder et al. 'Click' Chemistry in Polymer and Materials Science. Macromol. Rapid Commun. 2007, 28, 15-54.*

(Continued)

Primary Examiner — Daniel Sullivan
Assistant Examiner — Peter Anthopolos (57) ABSTRACT The present disclosure relates to implantable medical devices having a non-bioabsorbable substrate and an amphiphilic coating covalently bonded to the substrate for reducing the inflammatory response to the device after implantation.

18 Claims, 2 Drawing Sheets (56) References Cited

U.S. PATENT DOCUMENTS

| | | |
|---|---|---|
| 2004/0185053 A1 | 9/2004 | Govindan |
| 2004/0209317 A1 | 10/2004 | Ting |
| 2005/0032081 A1 | 2/2005 | Ju et al. |
| 2005/0038472 A1 | 2/2005 | Furst |
| 2005/0148032 A1 | 7/2005 | Saxon et al. |
| 2005/0222427 A1 | 10/2005 | Sharpless et al. |
| 2005/0233389 A1 | 10/2005 | Ting et al. |
| 2006/0018948 A1 | 1/2006 | Guire et al. |
| 2006/0085033 A1 | 4/2006 | Criscuolo et al. |
| 2006/0108393 A1 | 5/2006 | Heinrich et al. |
| 2006/0110782 A1 | 5/2006 | Bertozzi et al. |
| 2006/0147963 A1 | 7/2006 | Barone et al. |
| 2006/0167116 A1* | 7/2006 | Uchegbu et al. ............ 514/777 |
| 2006/0193865 A1 | 8/2006 | Govindan |
| 2006/0228300 A1 | 10/2006 | Chang et al. |
| 2006/0228357 A1 | 10/2006 | Chang et al. |
| 2006/0240092 A1 | 10/2006 | Breitenkamp et al. |
| 2006/0276658 A1 | 12/2006 | Saxon et al. |
| 2007/0020620 A1 | 1/2007 | Finn et al. |
| 2007/0037964 A1 | 2/2007 | Saxon et al. |
| 2007/0060658 A1 | 3/2007 | Diaz et al. |
| 2007/0077564 A1 | 4/2007 | Roitman et al. |
| 2007/0086942 A1 | 4/2007 | Chang et al. |
| 2007/0087001 A1 | 4/2007 | Taylor et al. |
| 2007/0099251 A1 | 5/2007 | Zhang et al. |
| 2007/0122550 A1* | 5/2007 | Narayanan et al. ............ 427/213 |
| 2007/0140966 A1 | 6/2007 | Chang et al. |
| 2007/0178133 A1 | 8/2007 | Rolland |
| 2007/0178448 A1 | 8/2007 | Tsao et al. |
| 2007/0190597 A1 | 8/2007 | Agnew et al. |
| 2007/0244265 A1* | 10/2007 | Matyjaszewski et al. .... 525/376 |
| 2007/0244296 A1 | 10/2007 | Tomalia et al. |
| 2007/0249014 A1 | 10/2007 | Agnew et al. |
| 2007/0254006 A1 | 11/2007 | Loose et al. |
| 2007/0258889 A1 | 11/2007 | Douglas et al. |
| 2007/0269369 A1 | 11/2007 | Gegg et al. |
| 2007/0272122 A1 | 11/2007 | Lahann et al. |
| 2007/0275387 A1 | 11/2007 | Ju |
| 2007/0298006 A1 | 12/2007 | Tomalia et al. |
| 2008/0015138 A1 | 1/2008 | Hamilton et al. |
| 2008/0035243 A1 | 2/2008 | Breitenkamp et al. |
| 2008/0038472 A1 | 2/2008 | Suzuki et al. |
| 2008/0045686 A1 | 2/2008 | Meagher et al. |
| 2008/0050731 A1 | 2/2008 | Agnew et al. |
| 2008/0051562 A1 | 2/2008 | Chaikof et al. |
| 2008/0121657 A1 | 5/2008 | Voegele et al. |
| 2008/0138317 A1 | 6/2008 | Fung |
| 2008/0160017 A1 | 7/2008 | Baker et al. |
| 2008/0166363 A1 | 7/2008 | Govindan et al. |
| 2008/0171067 A1 | 7/2008 | Govindan et al. |
| 2008/0187956 A1 | 8/2008 | Carrico et al. |
| 2008/0199736 A1 | 8/2008 | Gadeken et al. |
| 2008/0200628 A1 | 8/2008 | Gadeken et al. |
| 2008/0207913 A1 | 8/2008 | Breitenkamp et al. |
| 2008/0214436 A1 | 9/2008 | Yu et al. |
| 2008/0214801 A1 | 9/2008 | Saxon et al. |
| 2008/0214831 A1 | 9/2008 | Sharpless et al. |
| 2008/0221043 A1 | 9/2008 | Harth et al. |
| 2008/0241856 A1 | 10/2008 | Wong et al. |
| 2008/0241892 A1 | 10/2008 | Roitman et al. |
| 2008/0242171 A1 | 10/2008 | Huang et al. |
| 2008/0248126 A1 | 10/2008 | Cheng et al. |
| 2008/0267878 A1 | 10/2008 | Robillard et al. |
| 2008/0283572 A1 | 11/2008 | Boyden et al. |
| 2008/0311412 A1 | 12/2008 | Fokin et al. |
| 2009/0012457 A1 | 1/2009 | Childers et al. |
| 2009/0018646 A1 | 1/2009 | Zhao |
| 2009/0053139 A1 | 2/2009 | Shi et al. |
| 2009/0054619 A1 | 2/2009 | Baker et al. |
| 2009/0061010 A1 | 3/2009 | Zale et al. |
| 2009/0069561 A1 | 3/2009 | Fokin et al. |
| 2009/0082224 A1 | 3/2009 | Haddleton et al. |
| 2009/0124534 A1 | 5/2009 | Reineke |
| 2009/0137424 A1 | 5/2009 | Tsao et al. |
| 2009/0181402 A1 | 7/2009 | Finn et al. |
| 2009/0182151 A1 | 7/2009 | Wu et al. |
| 2009/0202433 A1 | 8/2009 | Chang et al. |
| 2009/0214755 A1 | 8/2009 | Armani et al. |
| 2009/0220607 A1 | 9/2009 | Kiser et al. |
| 2009/0240030 A1 | 9/2009 | Ju et al. |
| 2009/0247651 A1 | 10/2009 | Kapiamba et al. |
| 2009/0250588 A1 | 10/2009 | Robeson et al. |
| 2009/0253609 A1 | 10/2009 | Fleury et al. |
| 2009/0259016 A1 | 10/2009 | Johnson et al. |
| 2009/0263468 A1 | 10/2009 | McAnulty et al. |
| 2009/0269277 A1 | 10/2009 | Chang et al. |
| 2009/0281250 A1 | 11/2009 | DeSimone et al. |
| 2009/0297609 A1 | 12/2009 | Shoichet et al. |
| 2009/0306310 A1 | 12/2009 | Wu et al. |
| 2009/0312363 A1 | 12/2009 | Bradner et al. |
| 2010/0011472 A1 | 1/2010 | Hugel et al. |
| 2010/0015046 A1 | 1/2010 | Govindan et al. |
| 2010/0021391 A1 | 1/2010 | Douglas et al. |
| 2010/0034862 A1 | 2/2010 | Laronde et al. |
| 2010/0047258 A1 | 2/2010 | Wang et al. |
| 2010/0048738 A1 | 2/2010 | Fleury et al. |
| 2010/0069578 A1 | 3/2010 | Faust et al. |
| 2010/0098640 A1 | 4/2010 | Cohen et al. |
| 2010/0121022 A1 | 5/2010 | Musa et al. |
| 2010/0159011 A1 | 6/2010 | Lian et al. |

FOREIGN PATENT DOCUMENTS

| | | |
|---|---|---|
| EP | 0490854 B1 | 9/1996 |
| EP | 1975230 A1 | 1/2008 |
| EP | 2090592 A1 | 8/2009 |
| FR | 2892419 A1 * | 4/2007 |
| WO | WO 00/62827 | 10/2000 |
| WO | WO 2004/054622 A1 | 7/2004 |
| WO | WO 2005/062854 A2 | 7/2005 |
| WO | WO 2005/079217 A2 | 9/2005 |
| WO | WO 2005/084180 A2 | 9/2005 |
| WO | WO 2005/084367 A2 | 9/2005 |
| WO | WO 2005/087818 A1 | 9/2005 |
| WO | WO 2005/113605 A1 | 12/2005 |
| WO | WO 2006/005046 A2 | 1/2006 |
| WO | WO 2006/012569 A1 | 2/2006 |
| WO | WO 2006/050262 A2 | 5/2006 |
| WO | WO 2006/065266 A2 | 6/2006 |
| WO | WO 2006/084202 A2 | 8/2006 |
| WO | WO 2006/086325 A2 | 8/2006 |
| WO | WO 2006/091894 A2 | 8/2006 |
| WO | WO 2006/107617 A2 | 10/2006 |
| WO | WO 2006/107786 A2 | 10/2006 |
| WO | WO 2006/107903 A2 | 10/2006 |
| WO | WO 2007/003054 A1 | 1/2007 |
| WO | WO 2007003054 A1 * | 1/2007 |
| WO | WO 2007/041394 A2 | 4/2007 |
| WO | WO 2007/041451 A2 | 4/2007 |
| WO | WO 2007/047668 A2 | 4/2007 |
| WO | WO 2007/142683 | 12/2007 |
| WO | WO 2008/000429 | 1/2008 |
| WO | WO 2008/004988 A1 | 1/2008 |
| WO | WO 2008/013618 A1 | 1/2008 |
| WO | WO 2008/031525 A1 | 3/2008 |
| WO | WO 2008/047057 A1 | 4/2008 |
| WO | WO 2008/075955 A2 | 6/2008 |
| WO | WO 2008/077406 A2 | 7/2008 |
| WO | WO 2008/108736 A1 | 9/2008 |
| WO | WO 2008/115694 A2 | 9/2008 |
| WO | WO 2008/120016 A1 | 10/2008 |
| WO | WO 2009/029242 A1 | 3/2009 |
| WO | WO 2009/064696 A1 | 5/2009 |
| WO | WO 2009/136853 A1 | 11/2009 |
| WO | WO 2009/140429 A2 | 11/2009 |
| WO | WO 2010/057080 | 5/2010 |

OTHER PUBLICATIONS

Bergbreiter et al. "Click"—Based Covalent Layer-by-Layer Assembly on Polyethylene Using Water-Soluble Polymeric Reagents. Macromolecules 2007, 40, 5337-5343.*

Wu, Yan, et al. "Synthesis and characterization of a novel amphiphilic chitosan-polylactide graft copolymer." Carbohydrate Polymers 59.2 (2005): 165-171.*

(56) References Cited

OTHER PUBLICATIONS

Miwa, Akio, et al. "Development of novel chitosan derivatives as micellar carriers of taxol." Pharmaceutical Research 15.12 (1998): 1844-1850.*
Liu, Chen-Guang, et al. "Linolenic acid-modified chitosan for formation of self-assembled nanoparticles." Journal of agricultural and food chemistry 53.2 (2005): 437-441.*
International Search Report, Application No. PCT/IB2010/000703 dated Feb. 16, 2011, 4 pages.
Q. Shi, et al., "The Immobilization of Proteins on Biodegradable Polymer Fibers via Click Chemistry", Biomaterials, 29, (2008), pp. 1118-1126.
Jérôme, et al., "Recent Advances in the Synthesis of Aliphatic Polyesters Ring-Opening Polymerization", Advanced Drug Delivery Reviews, 60, (2008), pp. 1056-1076.
Zhang, et al., "2-Azido-2-deoxycellulose: Synthesis and 1, 3-Dipolar Cycloaddition", Helvetica Chimica Acta, vol. 91, pp. 608-617 (2008).
R. Riva, et al., "Contribution of "Click Chemisty" to the Synthesis of Antimicrobial Aliphatic Copolyester", Polymer 49, (2008), pp. 2023-2028.
Baskin, et al., "Copper Free Click Chemistry for Dynamic In Vivo Imaging", PNAS, vol. 104, No. 43, (Oct. 23, 2007), pp. 16793-16797.
Codelli, et al., "Second Generation Difluorinated Cyclooctynes for Copper-Free Click Chemistry", J. Am. Chem. Soc., vol. 130, No. 34, (2008), pp. 11486-11493.
Sletton and Bertozzi, "A Hydrophilic Azacyclooctyne for Cu-free Click Chemistry", Org. Lett. (2008) 10(14), pp. 3097-3099.
Cazalis, et al., "Bioconjugate Chem.", 15 (2004), pp. 1005-1009.
Smith, et al., "Synthesis and Convenient Functionalization of Azide-labeled Diacyglycerol Analogues for Modular Access to Biologically Active Lipid Probes", Bioconjugate Chem, 19(9), (2008). pgs. 1855-1863.
Haridas, et al., "Design and Synthesis of Triazole-based Peptidedendrimers" Tetrahedron Letters, vol. 48, (2007), pp. 4719-4722.
Raghavan, et al., "Chemical Probes for Profiling Fatty Acid-associated Proteins in Living Cells", Bioorg. Med. Chem. Lett., 18 (2008), pp. 5982-5986.
LeDevedec, et al., "Separation of Chitosan Oligomers by Immobilized Metal Affinity Chromatography", J. Chromatogr A., 2008, 1194(2), pp. 165-171.
Hartgerink, et al., "Pepti-damphiphile Nanofibers: A Versatile Scaffold For the Preparation of Self Assembling Materials", PNAS, 2002; 99(2), pp. 5133-5138.
Van Berkel, et al., Cem Bio Chem, 8, (2007), pp. 1504-1508.
Nottelet, et al., Biomaterials, 27, (2006), pp. 4948-4954.
Skierka, et al., "The Influence of Different Acids and Pepsin on the Extractability of Collagen From the Skin of Baltic Cod (*Gadus morhua*)", Food Chemisty, 105, (2007), pp. 1302-1306.
Eastoe, "The Amino Acid Composition of Mammalian Collagen and Gelatin", vol. 61, (1955), pp. 589-600.
Sicherl, et al., "Orthogonally Protected Sugar Diamino Acids as Building Blocks for Linear and Branched Oligosaccharide Mimetics", Angew. Chem. Int. Ed. 44, (2005), pp. 2096-2099.
Laughlin, et al., "In Vivo Imaging of Membrane-Associated Glycans in Developing Zebrafish", Science, 320, (2008), pp. 664-667.
Worch and Wittmann, "Unexpected Formation of Complex Bridged Tetrazoles via Intramolecular 1,3-dipolar Cycloaddition of 1,2-0-cyanoalkylidene Derivatives of 3-azido-3-deoxy-D-allose", Carbohydrate Research, 343, (2008), pp. 2118-2129.
Witczak et al., "A Click Chemistry Approach to Glycomimetics: Michael addition of 2,3,4,6-tetra-*O*-acetyl-1-thio-β-D-glucopyranose to 4-deoxy-1,2-*O*-isopropylident-L-*glycero*-pent-4-enopyranos-3-ulose-a convenient route to novel 4-deoxy-(1→5)-5-*C*-thiodisaccharides", Carbohydrate Research, 342, (2007), 1929-1933.
Marra, et al., "Validation of the Copper(1)-Catalyzed Azide-Alkyne Coupling in Ionic Liquids, Synthesis of a Triazole-Linked C-Disaccharide as a Case Study", J. Org. Chem (2008), 73(6), pp. 2458-2461.
Srinivasachari, et al., "Versatile Supramolecular pDNA Vehicles via "Click Polymerization" of β-cyclodextrin with oligoethyleneamines", Biomaterials, 30, (2009), pp. 928-938.
Arora, et al., "A Novel Domino-click Approach for the Synthesis of Sugar Based Unsymmetrical bis-1,2,3-triazoles", Carbohydrate Research, 343, (2008), 139-144.
Chen, et al., "Synthesis of a $C_3$-symmetric (1→6)-*N*-acetyl-β-D-glucosamine Octadecasaccharide using Click Chemistry", Carbohydrate Research, 340, (2005), pp. 2476-2482.
Gouin, et al., "Multi-Mannosides Based on a Carbohydrate Scaffold: Synthesis, Force Field Development, Molecular Dynamics Studies, and Binding Affinities for Lectin Con A", J. Org. Chem., 2007, 72(24), pp. 9032-9045.
Srinivasachari, etal., "Effects of Trehalose Click Polymer Length on pDNA Complex Stability and Delivery Efficacy", Biomaterials, 28, (2007), pp. 2885-2898.
Godeau, et al., Lipid-Conjugated Oligonucleotides via "Click Chemistry" Efficiently Inhibit Hepatitis C Virus Translation, J. med. Chem., 2008, 51(15), pp. 4374-4376.
Zou et al., "Cu-free Cycloaddition for Identifying Catalytic Active Adenylation Domains of Nonribosomal Peptide Synthesis by phage display", Bioorganic & Medicinal Chemistry Letters, 18 (2008), pp. 5664-5667.
Cantel, et al., "Synthesis and Conformational Analysis of a Cyclic Peptide Obtained via *i* to *i*+4 Intramolecular Side-chain to Side-chain Azide-Alkyne 1,3-Dipolar Cycloaddition" J. Org. Chem., 2008, 73 (15), pp. 5663-5674.
Dijk, et al., "Synthesis of Peptide-Based Polymers by Microwave-Assisted Cycloaddition Backbone Polymerization," Biomacro molecules, 2007, 8(2), pp. 327-330.
Köster, et al., "Spectroscopic and Electrochemical Studies of Ferroceryl Triazole Amino Acid and Peptide Bioconjugates Synthesized by Click Chemistry", Organometallics, 2008, 27(23) pp. 6326-6332.
Dijk, et al., "Synthesis and Characterization of Biodegradable Peptide-Baed Polymers Prepared by Microwave-Assisted Click Chemistry", Biomacromolecules, 2008, 9(10), pp. 2834-2843.
Jiang, et al., "Amphiphilic PEG/alkyl-grafted comb polylactides", J. Polymer Science Part B: Polymer Physics, 45(22), 2007, pp. 5227-5236.
Ochs, et al., "Low-Fouling, Biofunctionalized, and Biodegradeable Click Capsules", Biomacromolecules, 2008, 9(12), pp. 3389-3396.
Beatty and Tirrell, "Two-color Labeling of Temporally Defined Protein Populations in Mammalian Cells", Bioorg. Med. Chem. Lett., 18 (2008), pp. 5995-5999.
Sei-Ichi Aiba, "Stuides on Chitosan/Reactivity of partially N-acetylated Chitosan in Aqueous Media", Makromolekulare Chemie, Huthig and wepf verlag basel, ch, XP 000334528.

* cited by examiner

MEDICAL DEVICE WITH INFLAMMATORY RESPONSE-REDUCING COATING

RELATED APPLICATIONS

This application claims the benefit of U.S. Provisional Patent Application No. 61/154,385 filed Feb. 21, 2009.

BACKGROUND

1. Technical Field

The present disclosure relates to methods of making implantable medical devices having a coating that reduces inflammatory response to the implantable medical device.

2. Background of Related Art

Implantable medical devices are formed from a variety of different biodegradable and non-biodegradable materials. Non-biodegradable devices offer increased strength and support however, the permanency of these devices can induce inflammatory responses over the short and long term which affects the durability of the repair. Regarding long term performances non-absorbable polymer devices can induce chronic inflammatory responses which increase the risk of infection.

Accordingly, it would be beneficial to provide a medical device which includes a coating that reduces inflammatory response to the device.

SUMMARY

Implantable medical devices are described herein which include a non-bioabsorbable polymeric substrate having a surface to which a inflammatory response-reducing coating is attached. The inflammatory response-reducing coating includes an amphiphilic compound—that is, a compound having a hydrophilic portion and a hydrophobic portion. The hydrophobic portion of the amphiphilic compound is functionalized with a reactive member that reacts with a reactive member on a functionalized surface of the bioabsorbable polymeric substrate. In this manner, the hydrophobic portion of the amphiphilic compound is covalently bound to a surface of the implantable medical device.

Methods of making such medical devices are described herein which include reacting a functionalized surface of the non-bioabsorbable polymeric substrate with an amphiphilic compound having a functionalized hydrophobic portion. In embodiments, the surface of the non-bioabsorbable polymeric substrate and the hydrophobic portion of the amphiphilic compound are functionalized with reactive members involved in click chemistry.

DETAILED DESCRIPTION OF PREFERRED EMBODIMENTS

Implantable medical devices in accordance with the present disclosure include a non-bioabsorbable polymeric substrate having a surface to which a inflammatory response-reducing coating containing an amphiphilic compound is covalently bound. At least a portion of a surface of the non-bioabsorbable polymeric substrate is functionalized with a first reactive member and the hydrophobic portion of the amphiphilic compound is functionalized with a second reactive member that is reactive with the first reactive member on the surface of the non-bioabsorbable polymeric substrate. The first and second reactive members react to covalently bond the hydrophobic portion of the amphiphilic compound to the surface of the non-bioabsorbable polymeric substrate.

Figure 1:
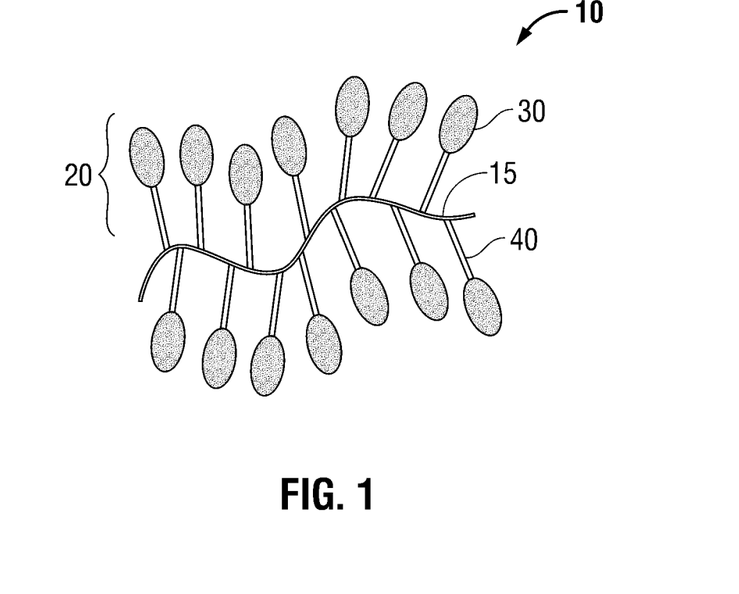
FIG. 1 schematically illustrates a medical device in accordance with an embodiment described herein.

Turning now to FIG. 1, medical device 10, has a non-bioabsorbable polymeric substrate shown as a single fiber or monofilament 15 having coating 20 that includes an amphiphilic compound having hydrophilic portion 30 and hydrophobic portion 40 wherein hydrophobic portion 40 is covalently attached to substrate 15. Hydrophilic portion 30 of amphiphilic coating 20 is positioned away from substrate 15 and provides an environment favorable for cellular attachment and infiltration. Hydrophobic portion 40 is positioned nearest substrate 15 and provides a barrier preventing water diffusion and also cell attraction to substrate 15, thereby retarding the degradation of medical device 10 and increasing the in vivo persistence of medical device 10.

Figure 2:
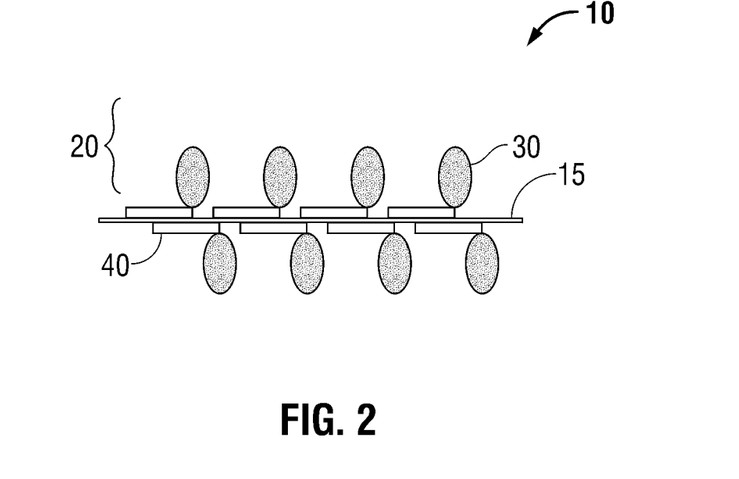
FIG. 2 schematically illustrates the effect of implantation on the embodiment of FIG. 1.

As shown in FIG. 2, hydrophobic portion 40 of amphiphilic compound 20 collapses along the surface of substrate 15 following implantation and prevents cellular migration during the early stages of the healing process and thereby reducing any inflammatory response. By limiting the inflammatory response during the early phases of the healing process, the long term performance of the implant is improved.

The Polymeric Substrate

The substrate of the medical devices described herein may be made from any non-bioabsorbable polymer. The non-bioabsorbable polymer may be a homopolymer or a copolymer, including random copolymer, block copolymer, or graft copolymer. The non-bioabsorbable polymer may be a linear polymer, a branched polymer, or a dendrimer. The non-bioabsorbable polymers may be of natural or synthetic origin. Examples of suitable non-bioabsorbable polymers include, but are not limited to fluorinated polymers (e.g. fluoroethylenes, propylenes, fluoroPEGs), polyolefins such as polyethylene, polyesters such as poly ethylene terepththalate (PET), polypropylene, cellulose, polytetrafluoroethylene (PTFE), nylons, polyamides, polyurethanes, silicones, ultra high molecular weight polyethylene (UHMWPE), polybutesters, polyaryletherketone, copolymers and combinations thereof.

The non-bioabsorbable polymeric substrate may be fabricated into any desired physical form. The polymeric substrate may be fabricated for example, by spinning, casting, molding or any other fabrication technique known to those skilled in the art. The polymeric substrate may be made into any shape, such as, for example, a fiber, sheet, rod, staple, clip, needle, tube, foam, or any other configuration suitable for a medical device. Where the polymeric substrate is in the form of a fiber, the fiber may be formed into a textile using any known technique including, but not limited to, knitting, weaving, tatting and the like. It is further contemplated that the polymeric substrate may be a non-woven fibrous structure.

The present non-bioabsorbable polymeric substrate having a coating containing an amphiphilic compound may be used as any medical device suitable for implantation. Some non-limiting examples include monofilaments, multifilaments, surgical meshes, ligatures, sutures, staples, patches, slings, foams, pellicles, films, barriers, and the like.

The Amphiphilic Compound

The amphiphilic compound includes at least one portion which is hydrophilic and at least one portion which is hydrophobic. The terms "hydrophilic" and "hydrophobic" are generally defined in terms of a partition coefficient P, which is the ratio of the equilibrium concentration of a compound in an organic phase to that in an aqueous phase. A hydrophilic compound has a log P value less than 1.0, typically less than about −0.5, where P is the partition coefficient of the compound between octanol and water, while hydrophobic compounds will generally have a log P greater than about 3.0, typically greater than about 5.0.

The amphiphilic compound may be linear, branched, block or graft copolymers. The hydrophilic portions are derived from hydrophilic polymers or compounds selected from the member consisting of polyamides, polyethylene oxide, hydrophilic polyurethanes, polylactones, polyimides, polylactams, poly-vinyl-pyrrolidone, polyvinyl alcohols, polyacrylic acid, polymethacrylic acid, poly(hydroxyethyl methacrylate), gelatin, dextran, oligosaccharides, such as chitosan, hyaluronic acid, alginate, chondroitin sulfate, mixtures and combinations thereof. The hydrophobic portions are derived from hydrophobic polymers or compounds selected from the member consisting of polyethylene, polypropylene, hydrophobic polyurethanes, polyacrylates, polymethacrylates, fluoropolymers, polycaprolactone, polylactide, polyglycolide, phospholipids, and polyureas, poly(ethylene/-vinyl acetate), polyvinylchloride, polyesters, polyamides, polycarbonate, polystyrenes, polytetrafluoroethylene, silicones, siloxanes, fatty acids, and chitosan having high degrees of acetylation and mixtures and combinations thereof. The amphiphilic compound may include any biocompatible combination of hydrophilic and hydrophobic portions.

In embodiments, the amphiphilic compound may include a hydrophobic portion derived from a fatty acid, some non-limiting examples include saturated fatty acids, monoenoic fatty acids, polyenoic fatty acids, methylene-interrupted polymethylene-interrupted, conjugated, allenic acids, cumulenic acids, acetylenic fatty acids, hydroxy fatty acids, dicarboxylic acids, fatty acid carbonates, divinyl ether fatty acids, sulfur containing fatty acids, fatty acid amides, methoxy and acetoxy fatty acids, keto fatty acids, aldehydic fatty acids, halogenated fatty acids (F, Cl, Br), nitrated fatty acids, arsenic containing fatty acids, branched-chain fatty acids, mono or multibranched chain fatty acids, branched methoxy fatty acids, branched hydroxy fatty acids, ring containing fatty acids, cyclopropane acids, cyclobutane acids, cyclopentenyl acids, furanoid acids, cyclohexyl acids, phenylalkanoic acids, epoxy acids, cyclic fatty peroxides, lipoic acids and combinations thereof. Examples of saturated fatty acids include butanoic, pentanoic, hexanoic, octanoic, nonanoic, decanoic, dodecanoic, tetradecanoic, hexadecanoic, heptadecanoic, octadecanoic, eicosanoic, docosanoic, tetracosanoic, hexacosanoic, heptacosanoic, and octacosanoic. In embodiments, the fatty acid may include one of the following formulas: $C_6H_{11}O$, $C_{10}H_{19}O$, $C_{16}H_{31}O$, $C_{22}H_{43}O$. The amphiphilic compound may also includes a hydrophilic portion derived from an oligosaccharide such as chitosan, hyaluronic acid, alginates or chondroitin sulfate.

Chitosan is a natural polysaccharide comprising copolymers of glucosamine and N-acetylglucosamine, and can be obtained by the partial acetylation of chitin, from crustacean shells, the second most abundant natural polymer after cellulose. The process of acetylation involves the removal of acetyl members from the molecular chain of chitin, leaving behind a complete amino member (—$NH_2$) and chitosan versatility depends mainly on this high degree chemical reactive amino members. As the degree of acetylation increases, the more hydrophobic the chitosan becomes. Conversely, as the degree of acetylation decreases, the more hydrophilic the chitosan becomes. Thus, in some embodiments, chitosan oligomers displaying different degrees of acetylation may be combined to form an amphiphilic compound. Moreover, in some embodiments in which more than one oligosaccharide may be utilized to form the amphiphilic compound, the degree of acetylation of the chitosan oligomers may be altered depending ion the hydrophilicity of the other oligosaccharides. For instance, the amphiphilic compound may include a hydrophilic portion derived from a chitosan oligomer having a low degree of acetylation, ranging from about 0 to about 50%, and a hydrophobic portion derived from a chitosan oligomer having a higher degree of acetylation, greater than about 50%. Alternatively, the amphiphilic compound may be formed under a raised pH, greater than 7.5, such that the compound includes a hydrophobic portion derived from a chitosan oligomer having a low degree of acetylation, ranging from about 0 to about 50%, and a hydrophilic portion derived from a hyaluronic acid oligomer or alginate oligomer which under the raised pH conditions displays a negative charge. Under the raised pH conditions, the chitosan oligomer having a low degree of acetylation displays a positive charge and becomes more hydrophilic.

In still other embodiments, a fatty acid hydrophobic portion may be combined with a hydrophilic drug. Some non-limiting examples of hydrophilic drugs include oxytocin, vasopressin, adrenocorticotrophic hormone (ACTH), epidermal growth factor (EGF), transforming growth factor antagonists, prolactin, luliberin or luteinizing hormone releasing hormone (LH-RH), LH-RH agonists or antagonists, growth hormone, growth hormone releasing factor, insulin, somatostatin, bombesin antagonists, glucagon, interferon, gastrin, tetragastrin, pentagastrin, urogastrone, secretin, calcitonin, enkephalins, endorphins, angiotensins, renin, bradykinin, bacitracins, polymyzins, colistins, tyrocidin, gramicidines, and synthetic analogues and modifications and pharmaceutically-active fragments thereof, monoclonal antibodies and soluble vaccines.

Coating the Polymer Substrate with the Amphiphilic Compound

In order to covalently bond the amphiphilic compound to the surface of the non-bioabsorbable polymeric substrate, the surface of the non-bioabsorbable polymeric substrate is functionalized with a first reactive member and the hydrophobic portion of the amphiphilic compound is functionalized with a second reactive member. The first and second reactive members are complementary. By "complementary" it is meant that the first and second reactive members are able to specifically interact together to covalently bond the amphiphilic compound to the functionalized polymer.

In embodiments, the surface of the non-bioabsorbable polymeric substrate and the hydrophobic portion of the amphiphilic compound are functionalized with electrophilic or nucleophilic functional members, such that, for example, a nucleophilic functional member on the surface of the non-bioabsorbable polymeric substrate may react with an electrophilic functional member on the hydrophobic portion of the amphiphilic compound to form a covalent bond.

Virtually any nucleophilic member can be used to functionalize the surface of the non-bioabsorbable polymeric substrate, so long as reaction can occur with the electrophilic member on the hydrophobic portion of the amphiphilic compound. Analogously, virtually any electrophilic member can be used to functionalize the hydrophobic portion of the amphiphilic compound, so long as reaction can take place with the nucleophilic member on the surface of the non-bioabsorbable polymeric substrate. The only limitation is a practical one, in that reaction between the complementary members should be fairly rapid and take place automatically upon admixture with an aqueous medium, without need for heat or potentially toxic or non-non-bioabsorbable reaction catalysts or other chemical reagents. It is also preferred although not essential that reaction occur without need for ultraviolet or other radiation. In embodiments, the reactions the complementary members should be complete in under 60 minutes, in embodiments under 30 minutes, in yet other embodiments, the reaction occurs in about 5 to 15 minutes or less.

Non-limiting examples of nucleophilic members include, but are not limited to, $-NH_2$, $-NHR$, $-N(R)_2$, $-SH$, $-OH$, $-COOH$, $-C_6H_4-OH$, $-PH_2$, $-PHR$, $-P(R)_2$, $-NH-NH_2$, $-CO-NH-NH_2$, $-C_5H_4N$, etc. wherein R is hydrocarbyl, typically $C_1$-$C_4$ alkyl or monocyclic aryl. Organometallic moieties are also useful nucleophilic members for the purposes of this disclosure, particularly those that act as carbanion donors. Examples of organometallic moieties include: Grignard functionalities $-RMgHal$ wherein R is a carbon atom (substituted or unsubstituted), and Hal is halo, typically bromo, iodo or chloro; and lithium-containing functionalities, typically alkyllithium members; sodium-containing functionalities.

It will be appreciated by those of ordinary skill in the art that certain nucleophilic members must be activated with a base so as to be capable of reaction with an electrophile. For example, when there are nucleophilic sulfhydryl and hydroxyl members on the surface of the non-bioabsorbable polymeric substrate, the composition must be admixed with an aqueous base in order to remove a proton and provide an $-S^-$ or $-O^-$ species to enable reaction with an electrophile. Unless it is desirable for the base to participate in the reaction, a non-nucleophilic base is used. In some embodiments, the base may be present as a component of a buffer solution.

The selection of electrophilic members provided on the hydrophobic portion of the amphiphilic compound is made so that reaction is possible with the specific nucleophilic members on the surface of the non-bioabsorbable polymeric substrate. Thus, when the surface of the non-bioabsorbable polymeric substrate is functionalized with amino members, the hydrophobic portion of the amphiphilic compound is functionalized with members selected so as to react with amino members. Analogously, when the surface of the non-bioabsorbable polymeric substrate is functionalized with sulhydryl moieties, the corresponding electrophilic members are sulfhydryl-reactive members, and the like.

By way of example, when the surface of the non-bioabsorbable polymeric substrate is functionalized with amino members (generally although not necessarily primary amino members), the electrophilic members present on the hydrophobic portion of the amphiphilic compound are amino reactive members such as, but not limited to: (1) carboxylic acid esters, including cyclic esters and "activated" esters; (2) acid chloride members ($-CO-Cl$); (3) anhydrides ($-(CO)-O-(CO)-R$); (4) ketones and aldehydes, including $\alpha,\beta$-unsaturated aldehydes and ketones such as $-CH=CH-CH=O$ and $-CH=CH-C(CH_3)=O$; (5) halides; (6) isocyanate ($-N=C=O$); (7) isothiocyanate ($-N=C=S$); (8) epoxides; (9) activated hydroxyl members (e.g., activated with conventional activating agents such as carbonyldiimidazole or sulfonyl chloride); and (10) olefins, including conjugated olefins, such as ethenesulfonyl ($-SO_2CH=CH_2$) and analogous functional members, including acrylate ($-CO_2-C=CH_2$), methacrylate ($-CO_2-C(CH_3)=CH_2$)), ethyl acrylate ($-CO_2-C(CH_2CH_3)=CH_2$), and ethyleneimino ($-CH=CH-C=NH$). Since a carboxylic acid member per se is not susceptible to reaction with a nucleophilic amine, components containing carboxylic acid members must be activated so as to be amine-reactive. Activation may be accomplished in a variety of ways, but often involves reaction with a suitable hydroxyl-containing compound in the presence of a dehydrating agent such as dicyclohexylcarbodiimide (DCC) or dicyclohexylurea (DHU). For example, a carboxylic acid can be reacted with an alkoxy-substituted N-hydroxy-succinimide or N-hydroxysulfosuccinimide in the presence of DCC to form reactive electrophilic members, the N-hydroxysuccinimide ester and the N-hydroxysulfosuccinimide ester, respectively. Carboxylic acids may also be activated by reaction with an acyl halide such as an acyl chloride (e.g., acetyl chloride), to provide a reactive anhydride member. In a further example, a carboxylic acid may be converted to an acid chloride member using, e.g., thionyl chloride or an acyl chloride capable of an exchange reaction. Specific reagents and procedures used to carry out such activation reactions will be known to those of ordinary skill in the art and are described in the pertinent texts and literature.

Analogously, when the surface of the non-bioabsorbable polymeric substrate is functionalized with sulfhydryl, the electrophilic members present on the hydrophobic portion of the amphiphilic compound are members that react with a sulfhydryl moiety. Such reactive members include those that form thioester linkages upon reaction with a sulfhydryl member, such as those described in PCT Publication No. WO 00/62827 to Wallace et al. As explained in detail therein, such "sulfhydryl reactive" members include, but are not limited to: mixed anhydrides; ester derivatives of phosphorus; ester derivatives of p-nitrophenol, p-nitrothiophenol and pentafluorophenol; esters of substituted hydroxylamines, including N-hydroxyphthalimide esters, N-hydroxysuccinimide esters, N-hydroxysulfosuccinimide esters, and N-hydroxyglutarinide esters; esters of 1-hydroxybenzotriazole; 3-hydroxy-3,4-dihydro-benzotriazin-4-one; 3-hydroxy-3,4-dihydro-quinazoline-4-one; carbonylimidazole derivatives; acid chlorides; ketenes; and isocyanates. With these sulfhydryl reactive members, auxiliary reagents can also be used to facilitate bond formation, e.g., 1-ethyl-3-[3-dimethylaminopropyl]carbodiimide can be used to facilitate coupling of sulfhydryl members to carboxyl-containing members.

In addition to the sulfhydryl reactive members that form thioester linkages, various other sulfydryl reactive functionalities can be utilized that form other types of linkages. For example, compounds that contain methyl imidate derivatives form imido-thioester linkages with sulfhydryl members. Alternatively, sulthydryl reactive members can be employed that form disulfide bonds with sulthydryl members, such members generally have the structure $-S-S-Ar$ where Ar is a substituted or unsubstituted nitrogen-containing heteroaromatic moiety or a non-heterocyclic aromatic member substituted with an electron-withdrawing moiety, such that Ar may be, for example, 4-pyridinyl, o-nitrophenyl, m-nitrophenyl, p-nitrophenyl, 2,4-dinitrophenyl, 2-nitro-4-benzoic acid, 2-nitro-4-pyridinyl, etc. In such instances, auxiliary reagents, i.e., mild oxidizing agents such as hydrogen peroxide, can be used to facilitate disulfide bond formation.

Yet another class of sulfhydryl reactive members forms thioether bonds with sulfhydryl members. Such members include, inter alia, maleimido, substituted maleimido, haloalkyl, epoxy, imino, and aziridino, as well as olefins (including conjugated olefins) such as ethenesulfonyl, etheneimino, acrylate, methacrylate, and ($\alpha,\beta$-unsaturated aldehydes and ketones.

When the surface of the non-bioabsorbable polymeric substrate is functionalized with —OH, the electrophilic functional members on the hydrophobic portion of the amphiphilic compound must react with hydroxyl members. The hydroxyl member may be activated as described above with respect to carboxylic acid members, or it may react directly in the presence of base with a sufficiently reactive electrophile such as an epoxide member, an aziridine member, an acyl halide or an anhydride.

When the surface of the non-bioabsorbable polymeric substrate is functionalized with an organometallic nucleophile such as a Grignard functionality or an alkyllithium member, suitable electrophilic functional members for reaction therewith are those containing carbonyl members, including, by way of example, ketones and aldehydes.

It will also be appreciated that certain functional members can react as nucleophiles or as electrophiles, depending on the selected reaction partner and/or the reaction conditions. For example, a carboxylic acid member can act as a nucleophile in the presence of a fairly strong base, but generally acts as an electrophile allowing nucleophilic attack at the carbonyl carbon and concomitant replacement of the hydroxyl member with the incoming nucleophile.

Table 1, below illustrates, solely by way of example, representative complementary pairs of electrophilic and nucleophilic functional members that may be employed in functionalizing the non-bioabsorbable polymeric substrate (e.g., $R_1$ in Table 1) and the hydrophobic portion of the amphiphilic compound (e.g., $R_2$ in Table 1).

In embodiments, the surface of the non-bioabsorbable polymeric substrate is functionalized with a first click-reactive member and the hydrophobic portion of the amphiphilic compound is functionalized with a second click-reactive member complementary to the first click-reactive member. The "click-reactive members" are meant to include those reactive members used in the processes known to those skilled in the art as Click chemistry.

Click chemistry refers to a collection of reactive members having a high chemical potential energy capable of producing highly selective, high yield reactions. The reactive members react to form extremely reliable molecular connections in most solvents, including physiologic fluids, and often do not interfere with other reagents and reactions. Examples of click chemistry reactions include Huisgen cycloaddition, Diels-Alder reactions, thiol-alkene reactions, and maleimide-thiol reactions.

Huisgen cycloaddition is the reaction of a dipolarophile with a 1,3-dipolar compound that leads to 5-membered (hetero)cycles. Examples of dipolarophiles are alkenes and alkynes and molecules that possess related heteroatom functional groups (such as carbonyls and nitriles). 1,3-Dipolar compounds contain one or more heteroatoms and can be described as having at least one mesomeric structure that represents a charged dipole. They include nitril oxides, azides, and diazoalkanes. Metal catalyzed click chemistry is an extremely efficient variant of the Huisgen 1,3-dipolar cycloaddition reaction between alkyl-aryly-sulfonyl azides, C—N triple bonds and C—C triple bonds which is well-

TABLE 1

| REPRESENTATIVE NUCLEOPHILIC COMPONENT (A, $FN_{NU}$) | REPRESENTATIVE ELECTROPHILIC COMPONENT (B, $FN_{EL}$) | RESULTING LINKAGE |
|---|---|---|
| $R^1$—$NH_2$ | $R^2$—O—(CO)—O—N(COCH$_2$) (succinimidyl carbonate terminus) | $R^1$—NH—(CO)—O—$R^2$ |
| $R^1$—SH | $R^2$—O—(CO)—O—N(COCH$_2$) | $R^1$—S—(CO)—O—$R^2$ |
| $R^1$—OH | $R^2$—O—(CO)—O—N(COCH$_2$) | $R^1$—S—(CO)—$R^2$ |
| $R^1$—$NH_2$ | $R^2$—O(CO)—CH=CH$_2$ (acrylate terminus) | $R^1$—NH—CH$_2$CH$_2$—(CO)—O—$R^2$ |
| $R^1$—SH | $R^2$—O—(CO)—CH=CH$_2$ | $R^1$—S—CH$_2$CH$_2$—(CO)—O—$R^2$ |
| $R^1$—OH | $R^2$—O—(CO)—CH=CH$_2$ | $R^1$—O—CH$_2$CH$_2$—(CO)—O—$R^2$ |
| $R^1$—$NH_2$ | $R^2$—O(CO)—(CH$_2$)$_3$—CO$_2$N(COCH$_2$) (succinimidyl glutarate terminus) | $R^1$—NH—(CO)—(CH$_2$)$_3$—(CO)—O$R^2$ |
| $R^1$—SH | $R^2$—O(CO)—(CH$_2$)$_3$—CO$_2$—N(COCH$_2$) | $R^1$—S—(CO)—(CH$_2$)$_3$—(CO)—O$R^2$ |
| $R^1$—OH | $R^2$—O(CO)—(CH$_2$)$_3$—CO$_2$—N(COCH$_2$) | $R^1$—O—(CO)—(CH$_2$)$_3$—(CO)—O$R^2$ |
| $R^1$—$NH_2$ | $R^2$—O—CH$_2$—CO$_2$—N(COCH$_2$) (succinimidyl acetate terminus) | $R^1$—NH—(CO)—CH$_2$—O$R^2$ |
| $R^1$—SH | $R^2$—O—CH$_2$—CO$_2$—N(COCH$_2$) | $R^1$—S—(CO)—CH$_2$—O$R^2$ |
| $R^1$—OH | $R^2$—O—CH$_2$—CO$_2$—N(COCH$_2$) | $R^1$—O—(CO)—CH$_2$—O$R^2$ |
| $R^1$—$NH_2$ | $R^2$—O—NH(CO)—(CH$_2$)$_2$—CO$_2$—N(COCH$_2$) (succinimidyl succinamide terminus) | $R^1$—NH—(CO)—(CH$_2$)$_2$—(CO)—NH—O$R^2$ |
| $R^1$—SH | $R^2$—O—NH(CO)—(CH$_2$)$_2$—CO$_2$—N(COCH$_2$) | $R^1$—S—(CO)—(CH$_2$)$_2$—(CO)—NH—O$R^2$ |
| $R^1$—OH | $R^2$—O—NH(CO)—(CH$_2$)$_2$—CO$_2$—N(COCH$_2$) | $R^1$—O—(CO)—(CH$_2$)$_2$—(CO)—NH—O$R^2$ |
| $R^1$—$NH_2$ | $R^2$—O—(CH$_2$)$_2$—CHO (propionaldehyde terminus) | $R^1$—NH—(CO)—(CH$_2$)$_2$—O$R^2$ |
| $R^1$—$NH_2$ |  (glycidyl ether terminus) | $R^1$—NH—CH$_2$—CH(OH)—CH$_2$—O$R^2$ and $R^1$—N[CH$_2$—CH(OH)—CH$_2$—O$R^2$]$_2$ |
| $R^1$—$NH_2$ | $R^2$—O—(CH$_2$)$_2$—N=C=O (isocyanate terminus) | $R^1$—NH—(CO)—NH—CH$_2$—O$R^2$ |
| $R^1$—$NH_2$ | $R^2$—SO$_2$—CH=CH$_2$ (vinyl sulfone terminus) | $R^1$—NH—CH$_2$CH$_2$—SO$_2$—$R^2$ |
| $R^1$—SH | $R^2$—SO$_2$—CH=CH$_2$ | $R^1$—S—CH$_2$CH$_2$—SO$_2$—$R^2$ | suited herein. The results of these reactions are 1,2 oxazoles, 1,2,3 triazoles or tetrazoles. For example, 1,2,3 triazoles are formed by a copper catalyzed Huisgen reaction between alkynes and alkyl/aryl azides. Metal catalyzed Huisgen reactions proceed at ambient temperature, are not sensitive to solvents, i.e., nonpolar, polar, semipolar, and are highly tolerant of functional groups. Non-metal Huisgen reactions (also referred to as strain promoted cycloaddition) involving use of a substituted cyclooctyne, which possesses ring strain and electron-withdrawing substituents such as fluorine, that together promote a [3+2] dipolar cycloaddition with azides are especially well-suited for use herein due to low toxicity as compared to the metal catalyzed reactions. Examples include DIFO and DIMAC. Reaction of the alkynes and azides is very specific and essentially inert against the chemical environment of biological tissues. One reaction scheme may be represented as:

a)

where R and R' are a polymeric substrate or a amphiphilic compound.

The Diels-Alder reaction combines a diene (a molecule with two alternating double bonds) and a dienophile (an alkene) to make rings and bicyclic compounds. Examples include:

The thiol-alkene (thiol-ene) reaction is a hydrothiolation, i.e., addition of RS—H across a C=C bond. The thiol-ene reaction proceeds via a free-radical chain mechanism. Initiation occurs by radical formation upon UV excitation of a photoinitiator or the thiol itself. Thiol-ene systems form ground state charge transfer complexes and therefore photopolymerize even in the absence of initiators in reasonable polymerization times. However, the addition of UV light increases the speed at which the reaction proceeds. The wavelength of the light can be modulated as needed, depending upon the size and nature of the constituents attached to the thiol or alkene. A general thiol-ene coupling reaction mechanism is represented below:

In embodiments, the surface of the non-bioabsorbable polymeric substrate and the hydrophobic portion of the amphiphilic compound are functionalized to include a first click-reactive member which is an alkyne and a second click-reactive member which is an azide, respectively. In embodiments, the surface of the non-bioabsorbable polymeric substrate and the hydrophobic portion of the amphiphilic compound are functionalized to include a first click-reactive member which is an azide and a second click-reactive member which is an alkyne, respectively.

The first and second click-reactive members are intended to react and covalently bond the amphiphilic compound to the functionalized surface of the non-bioabsorbable polymeric substrate at a physiologic pH. However, in some embodiments, the first and second click-reactive members may react quicker or more completely following the addition of a catalyst, such as a pH modifier, a metal ion catalyst or the introduction of heat or radiation. In embodiments, the addition of UV radiation may enhance the formation of a covalent bond between the first and second click-reactive members. In embodiments, the addition of a metal catalyst, e.g., transition metal ions such as copper ions, may assist with the formation of a covalent bond between the first and second click-reactive members.

Figure 3:
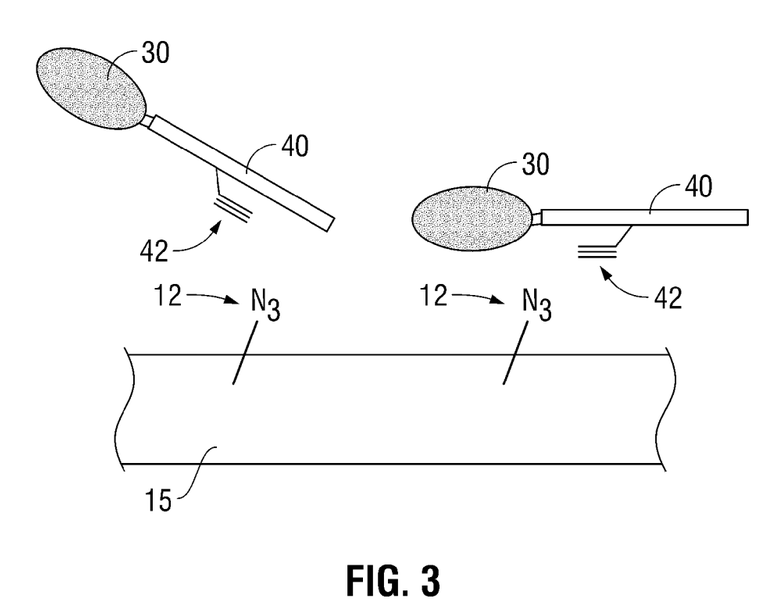
FIG. 3 schematically illustrates a medical device having an activated surface and an activated amphiphilic compound.

As shown in FIG. 3, non-bioabsorbable polymeric substrate 15 includes first reactive functional members, in this case azide members 12. An amphiphilic compound having hydrophilic portion 30 and hydrophobic portion 40 wherein hydrophobic portion 40 includes second reactive members, in this case alkyne members 42 are contacted with substrate 15 in solution under suitable reaction conditions. As those skilled in the art will recognize, reaction times between the azide and alkyne members can be reduced from about 24 hours at room temperature to mere seconds at room temperature by the presence of transition metal ions, such as copper ions.

Figure 4:
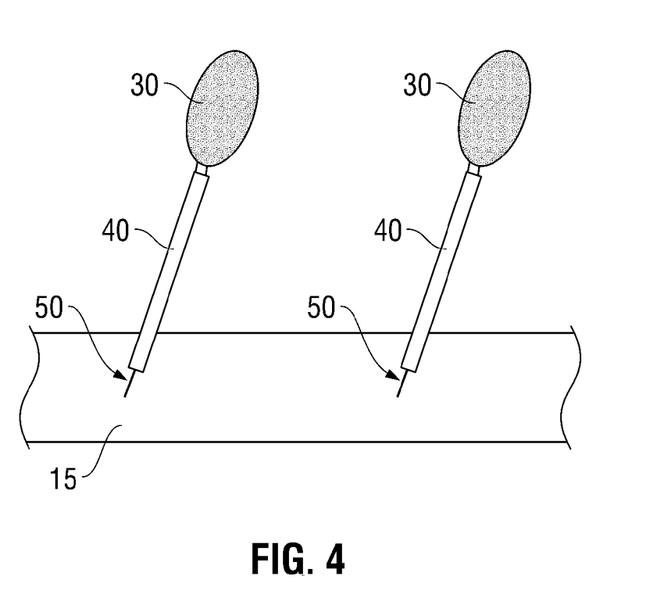
FIG. 4 schematically illustrates the medical device shown in FIG. 3 having the amphiphilic compound covalently bonded thereto.

As shown in FIG. 4, after reaction non-bioabsorbable polymeric substrate 15 includes a coating of the amphiphilic compound having hydrophilic portion 30 extending away from substrate 15 and hydrophobic portion 40 covalently bound to substrate 15 via a triazole linkage 50.

Functionalizing the Substrate and Amphiphilic Compound

The first and second reactive members may be positioned on the non-bioabsorbable polymeric substrate and amphiphilic compound using any variety of suitable chemical processes. With respect to the first reactive members on the non-bioabsorbable polymeric substrate, it is contemplated that a plurality of first reactive members may be present and may be terminally located, or alternatively located along the length of the polymer chain.

For example, the monomers from which the non-bioabsorbable polymeric substrate is made can be functionalized so that the reactive members appear along the length of the non-bioabsorbable polymer. In such embodiments, the monomers can be initially functionalized with a member such as a halogen to provide a reactive site at which the desired first reactive member can be attached after polymerization. For example, the halogenated polymer can be reacted with sodium azide to provide azide groups along the polymer chain or with propagyl alcohol to provide alkyne groups along the polymer chain. Alternatively, a pre-formed non-bioabsorbable polyester can be halogenated by reaction with a non-nucleophilic strong base, such as lithium diisopropylamide, followed by electrophilic substitution with iodine chloride. The halogenated polyester is then reacted with sodium azide or propagyl alcohol to provide azide or alkyne groups, respectively.

In other embodiments, the non-bioabsorbable polymeric substrate is functionalized after it has been fabricated into the desired form. For example, non-bioabsorbable polymeric fibers can be functionalized after the spinning process. In embodiments, the fibers are surface treated and then activated with the first reactive member (optionally with a coupling agent (e.g., a silane coupling agent) being used). Surface activation of non-bioabsorbable and biocompatible aliphatic polyesters can be achieved by acid or base hydrolysis, treatment by means of cold plasma, by chemical reactions or electromagnetic radiations. It is contemplated that such surface activation can be performed before or after the fibers are made into a textile structure.

Hydrolysis can be conducted in the presence of an aqueous solution of a base or an acid to accelerate surface reaction, inasmuch as excessively long processes of activation can induce a reduction in molecular weight and thus in the mechanical properties of the material. Suitable bases for obtaining watery solutions suited to the aim are, for example, strong alkalis, such as LiOH, Ba(OH)$_2$, Mg(OH)$_2$, NaOH, KOH, Na$_2$CO$_3$, Ca(OH)$_2$ and the weak bases, such as for example NH$_4$OH and the ammines such as methylamine, ethylamine, diethylamine and dimethylamine. Acids suitable for surface hydrolysis treatments can be chosen, for example, from among HCl, HClO$_3$, HClO$_4$, H$_2$SO$_3$, H$_2$SO$_4$, H$_3$PO$_3$, H$_3$PO$_4$, HI, HIO$_3$, HBr, lactic acid, glicolic acid. Surface activation by means of hydrolysis can be conducted at temperatures preferably comprised between 0 degrees Celsius and the material softening temperature. Plasma treatment can be carried out both in the presence of a reactive gas, for example air, Ar, O$_2$ with the formation of surface activation of oxygenate type, such as —OH, —CHO, —COOH.

Surface treatment, whether hydrolytic or with plasma, can remain unaltered or can be followed by further chemical modifications to provide the first reactive members on the non-bioabsorbable polymeric substrate. Thus, for example, the COONa members generated by a base hydrolysis can be subsequently converted into COOH members by treatment with strong mineral acids. Further, the surface freeing of alcoholic members by means of a hydrolysis process can be followed by reaction by means of the addition of a compound provided with functional member or members able to react with surface alcoholic members, such as for example by means of the addition of an anhydride such as succinic anhydride, with the conversion of —OH members into —O—CO—CH$_2$—CH$_2$—COOH members. Suitable surface activation techniques are disclosed in U.S. Pat. No. 6,107,453, the entire disclosure of which is incorporated herein by this reference.

With respect to the hydrophobic portion of the amphiphilic compound, it is contemplated that one or more than one second reactive members can be provided thereon. The process used to incorporate the second reactive members on the hydrophobic portion of the amphiphilic compound will be chosen based upon the nature of the hydrophobic portion.

For example, where the hydrophobic portion is based on a fatty acid, the second reactive members can be attached using the following synthetic route:

Scheme 1. Synthetic Route to Head Group Azide-Tagged Diacyglycerol Scaffold 2

-continued

In other embodiments where the hydrophobic portion is based on a hydrophobic peptide azide groups may be provided by conversion of the amino acid methyl ester to the corresponding azide via a Cu(II)-catalyzed diazotransfer reaction using triflic azide as shown in the following reaction scheme:

In yet other embodiments where the hydrophobic portion is based on an oligosaccharide, the second reactive members can be attached using the following reaction scheme as described in detail in Zhang et al., Helvetica Chimica Acta—Vol. 91 pages 608-617 (2008):

In embodiments, the acids used to introduce the acyl chains (10d) may be dicarboxylic acid fatty acids which provide for the synthesis of di-azide compounds.

In other embodiments where the hydrophobic portion is based on a hydrophobic peptide, N-propargyl maleimide can be used to attach alkyne group (the second reactive members) on to the protein using to the thiol group as shown below:

In embodiments, a plurality of different reactive members may be positioned on each of the non-bioabsorbable polymeric substrate and amphiphilic compound.

Various modifications and variations of the polymers, amphiphilic compounds, medical devices, click-reactive members and processes described herein will be apparent to those skilled in the art from the foregoing detailed description. Such modifications and variations are intended to come within the scope of the following claims.

What is claimed is:

1. A medical device comprising:
a substrate comprising a graft polymer, wherein the main chain of the graft polymer is non-bioabsorbable and is selected from the group consisting of polyethylene terephthalate, polypropylene, polytetrafluoroethylene, a nylon, a polyurethane, a silicone, an ultra-high molecular weight polyethylene, a polybutester, a polyaryletherketone, and copolymers and combinations thereof; and an amphiphilic polymer comprising both:
(1) a hydrophilic domain composed of chitosan having a degree of acetylation that is less than or equal to 50%, the hydrophilic domain having an octanol-water partition coefficient (log $P_{OW}$) of less than 1.0; and
(2) a hydrophobic domain composed of chitosan having a degree of acetylation that is greater than 50%, the hydrophobic domain having an octanol-water partition coefficient (log $P_{OW}$) of greater than 5; and
wherein the hydrophobic domain is covalently bonded to a side chain of the graft polymer via a triazole linkage.

2. The medical device of claim 1, wherein the triazole linkage is produced by cyclization of an azide and an alkyne.

3. The medical device of claim 1, wherein the main chain of the graft polymer is composed of polyethylene terephthalate.

4. The medical device of claim 1, wherein the main chain of the graft polymer is composed of polypropylene.

5. The medical device of claim 1, wherein the hydrophilic domain favors cellular attachment.

6. The medical device of claim 1, wherein the hydrophobic domain provides a barrier.

7. The medical device of claim 1, wherein the medical device is a monofilament.

8. The medical device of claim 1, wherein the medical device is a multifilament.

9. The medical device of claim 1, wherein the medical device is a surgical mesh.

10. The medical device of claim 1, wherein the medical device is a ligature.

11. The medical device of claim 1, wherein the medical device is a suture.

12. The medical device of claim 1, wherein the medical device is a staple.

13. The medical device of claim 1, wherein the medical device is a patch.

14. The medical device of claim 1, wherein the medical device is a sling.

15. The medical device of claim 1, wherein the medical device is a foam.

16. The medical device of claim 1, wherein the medical device is a pellicle.

17. The medical device of claim 1, wherein the medical device is a film.

18. The medical device of claim 1, wherein the medical device is a barrier.

* * * * *